United States Patent
von Schuckmann

(10) Patent No.: US 8,210,170 B2
(45) Date of Patent: Jul. 3, 2012

(54) MANUAL INHALATOR FOR POWDERED SUBSTANCES

(76) Inventor: Alfred von Schuckmann, Kevelaer (DE)

( * ) Notice: Subject to any disclaimer, the term of this patent is extended or adjusted under 35 U.S.C. 154(b) by 2035 days.

(21) Appl. No.: 10/522,402

(22) PCT Filed: Jun. 30, 2003

(86) PCT No.: PCT/EP03/06942
§ 371 (c)(1),
(2), (4) Date: Oct. 7, 2005

(87) PCT Pub. No.: WO2004/009168
PCT Pub. Date: Jan. 29, 2004

(65) Prior Publication Data
US 2008/0092885 A1     Apr. 24, 2008

(30) Foreign Application Priority Data
Jul. 22, 2002 (DE) .................................. 102 33 150

(51) Int. Cl.
*A61M 16/00* (2006.01)
*A61M 16/10* (2006.01)
(52) U.S. Cl. .......... 128/203.15; 128/203.12; 128/200.24
(58) Field of Classification Search ............. 128/200.24, 128/203.12, 203.15, 200.11–200.22; 222/209, 222/354, 385, 401, 402, 630, 631; 239/369
See application file for complete search history.

(56) References Cited

U.S. PATENT DOCUMENTS

| | | | | |
|---|---|---|---|---|
| 4,132,332 A | * | 1/1979 | Wassilieff | 222/387 |
| 5,323,936 A | * | 6/1994 | Wolter et al. | 222/401 |
| 5,676,289 A | * | 10/1997 | Gross et al. | 222/494 |

FOREIGN PATENT DOCUMENTS

| | | |
|---|---|---|
| DE | C 44 15 462 | 8/1995 |
| DE | 199 63 946 C2 | 3/2001 |
| DE | 19963946 A1 * | 3/2001 |
| EP | 0 652 022 | 5/1995 |
| EP | 0561 838 | 10/1996 |
| WO | WO 90/07351 | 7/1990 |
| WO | WO 01 15760 | 3/2001 |
| WO | WO01/15760 A1 * | 3/2001 |

* cited by examiner

*Primary Examiner* — Annette Dixon
(74) *Attorney, Agent, or Firm* — Lucas & Mercanti, LLP; Klaus P. Stoffel

(57) ABSTRACT

Manually actuable inhaler (1) for pulverulent substances, during manual actuation, apportions a defined discharge quantity (20') from a substance storage quantity (20) in a metering chamber (D) upstream of a discharge passage (21), for providing an airborne. discharge from a mouthpiece opening (14). The inhaler has a piston (8) which generates the discharge airstream, together with a cavity (17) in a body portion (15) of the piston, the cavity forming a substance storage chamber (SV) and the metering chamber (D). A reduced pressure, which is generated during a return stroke of the piston (8), opens the metering chamber (D) toward the substance storage quantity (20). The base of the metering chamber (D), is formed by an air-permeable membrane and the chamber is closed by a valve cone (65).

4 Claims, 13 Drawing Sheets

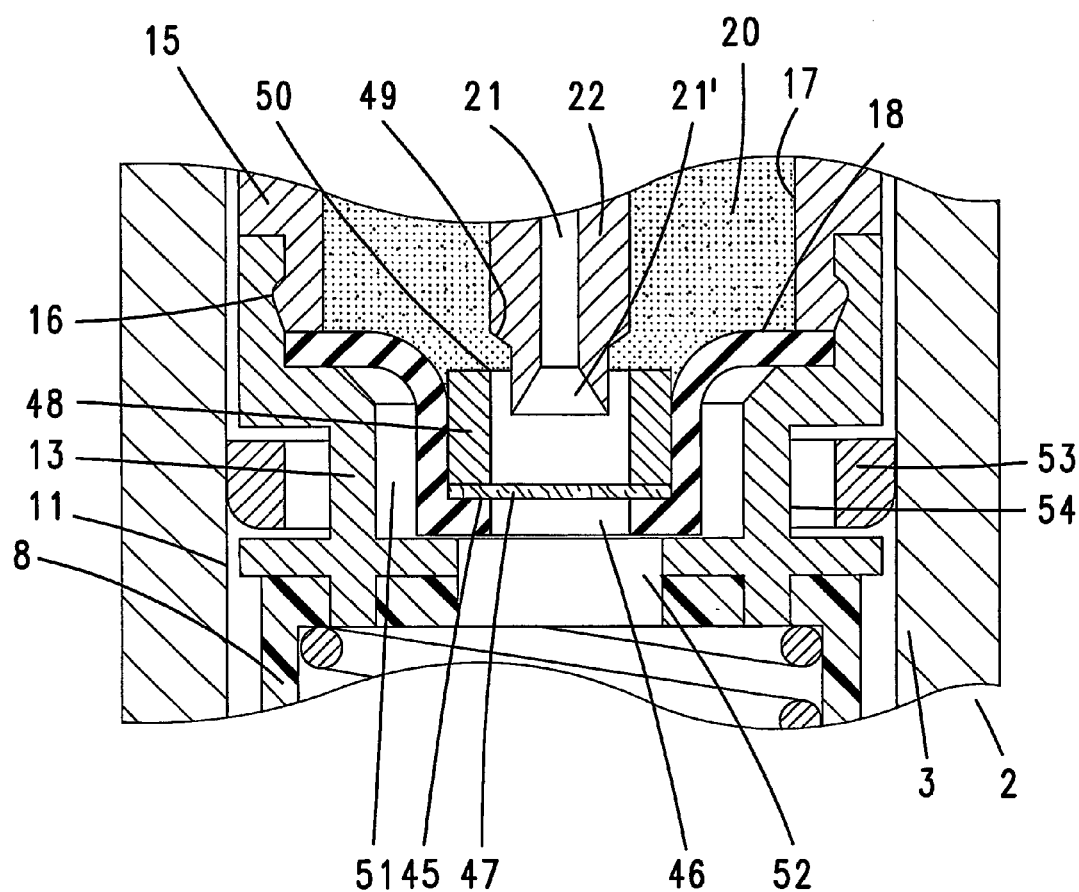

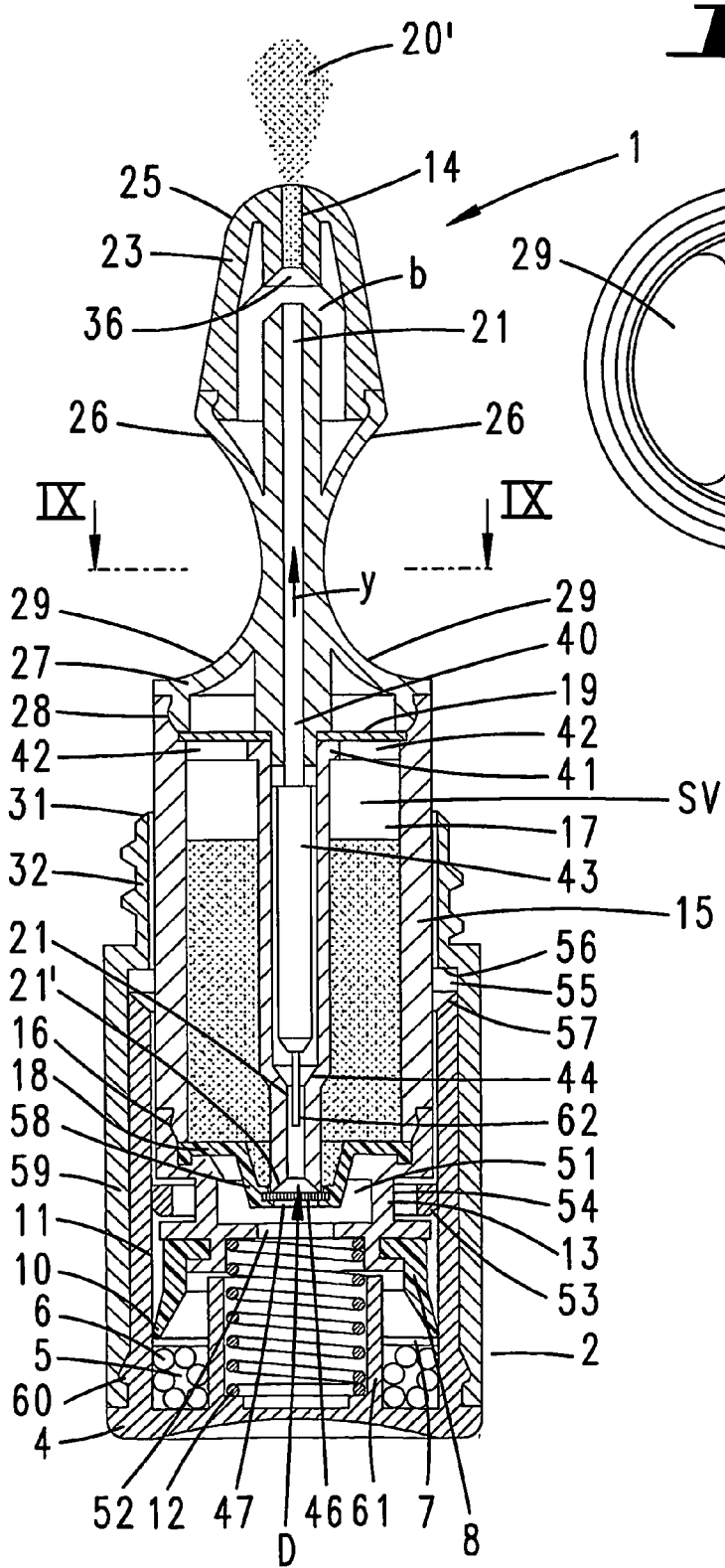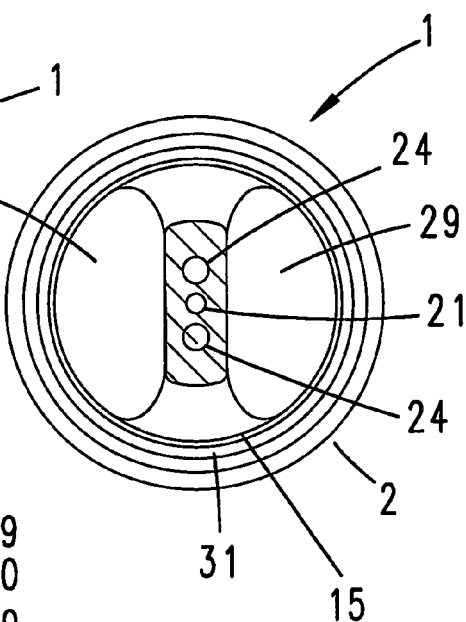

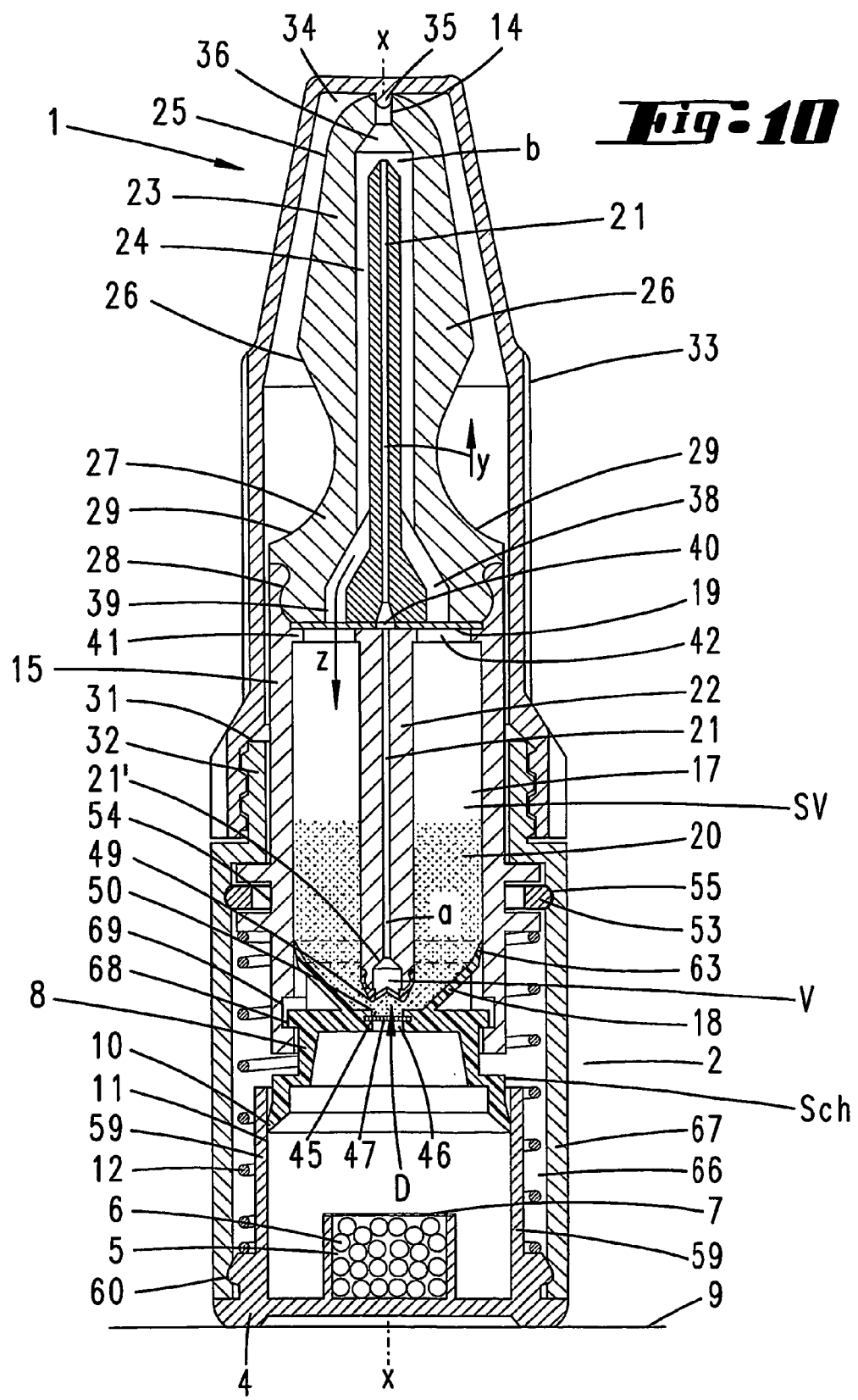

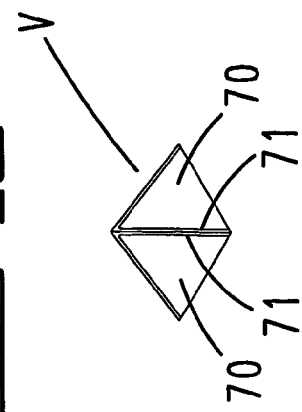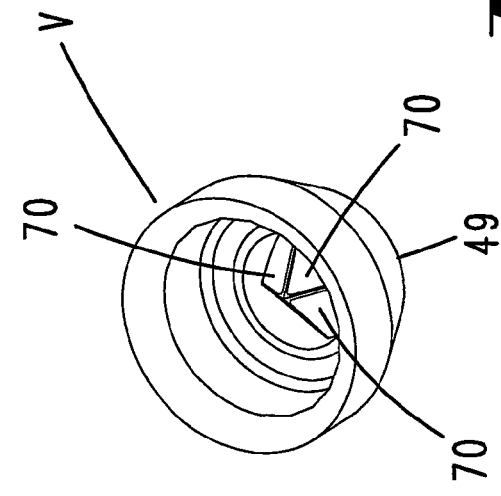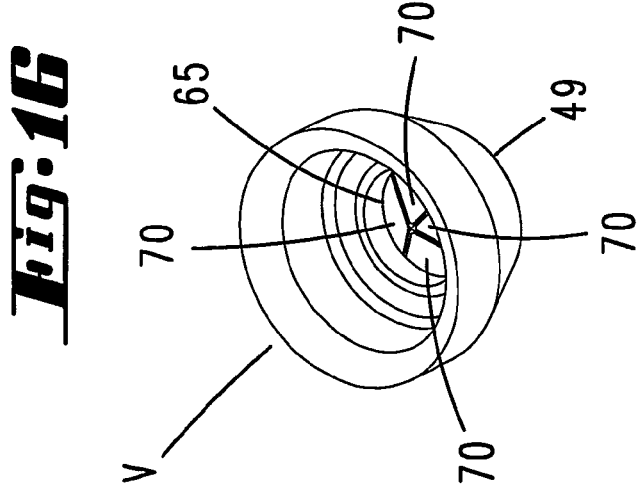

MANUAL INHALATOR FOR POWDERED SUBSTANCES

FIELD AND BACKGROUND OF THE INVENTION

The invention relates to a manually actuable inhaler for pulverulent substances, in particular medicinal substances, in which, during the manual actuation, a defined discharge quantity from a substance storage quantity is apportioned out in a metering chamber upstream of a discharge passage for the purpose of airborne discharge from a mouthpiece opening at the end of the discharge passage, a piston which generates the discharge airstream, together with a cavity of its body portion, forming a substance storage chamber and the metering chamber, a reduced pressure which is generated during the return stroke of the piston opening toward the substance storage quantity, and furthermore the base of the metering chamber being formed by an air-permeable membrane.

DE-C 44 15 462 and EP 0 561 838 have disclosed application aids for pulverulent substances in the form of an inhaler which is conceived for emptying by a mouth sucking action. Depending on the user's constitution, the suction force generally differs extensively according to the particular individual.

WO 90/07351 has disclosed an inhaler in which the emptying of the metering chamber is effected by a pump/cylinder unit.

The administration of pulverulent substances, in particular of medicaments, requires not only a fine distribution in the transporting airstream but also that this airstream should always emerge with the same power, the latter as far as possible being stronger than that which a patient usually exerts or can exert by sucking. Only then can the pulverulent material reliably reach its intended destination. In this context, it is also necessary for the quantities to be precisely reproducible. This also requires, inter alia, that the pulverulent substance, i.e. the substance storage quantity, should not form a blockage. Furthermore, with regard to pump piston solutions, it is important to control the unpleasant effects of sudden bursts. Although it should be possible to apply a powerful transporting airstream, this airstream must not be excessive.

SUMMARY OF THE INVENTION

The present invention is based on the subject matter of DE 199 63 946 C2.

It is an object of the invention to provide an inhaler of the generic type in a functionally reliable manner which is advantageous for use with regard to the objectives and stipulations which have been described.

This object is achieved first and foremost with a manually actuated inhaler having the features of claim 1, in which, in addition to the combination of features, it is provided that the airstream volume which results from the piston movement amounts to more than one hundred times but less than six hundred times the volume of the metering chamber. This leads to a powerful but not sudden airstream which transports the pulverulent substance in a finely distributed form. The powder particle density is excellently matched to the airstream volume. At the same time, relatively strong mechanical loads on the air-permeable membrane are avoided. The service life of an inhaler of this type is increased. It is preferable for the airstream volume to be four hundred times the volume of the metering chamber. 10 mg of pulverulent substance are taken up in approx. 4 ml of airstream. The volume of the metering chamber is in this case 10 $mm^3$. In addition, there are also retained features and properties of the basic version of the generic type. For example, the pulverulent substance is accommodated in a moving component of the inhaler, namely the body portion of the piston. The substance therefore always moves with it. In addition to this, as it were, mechanical vibratory device (both the advancing movement and the vibratory movement are utilized), a slipping movement of the pulverulent substance is also generated by the refilling of the metering chamber in each instance. A discharge compressed airstream passes over the powder-filled cavity of the metering chamber and a reduced air pressure opens the chamber. Therefore, blockage of the pulverulent substance is virtually ruled out. The airstream is always applied with the same strength. In this context, it is possible to utilize the relatively large piston cross section in relation to the discharge passage, which in relative terms is of smaller cross section and upstream of which the flow-inhibiting barrier of the air-permeable membrane is connected. Furthermore, it is proposed that the body portion at an opposite end from the piston, forms the mouthpiece opening. This mouthpiece opening can be optimally shaped with regard to the airstream. Furthermore, it has proven expedient for the discharge passage to be configured as a piston body portion inner tube, which extends in the center of the body portion of the piston—the piston being under spring loading—and the discharge quantity collecting beneath the piston-side end of the inner tube. A central system of this kind creates an annular access space for the pulverulent substance, which in turn is also beneficial for the desired accuracy of metering. Furthermore, it has proven expedient if the manually actuated piston spring loading stroke is the discharge stroke and the discharge quantity accumulates during the spring-triggered return stroke of the piston. Therefore, the discharge quantity is formed virtually automatically. A quantity which is ready for discharge is always available right until the end. An advantageous metering chamber is achieved if the discharge quantity collects in a recess in the base of the substance storage chamber and the upper edge of the recess alternates between a sealing position and an opening position of the piston body portion inner tube. The edge of the recess in the metering chamber may move indirectly or directly onto the piston body portion inner tube, in such a manner as to block access. On account of the internal elasticity, it is advantageously returned to the sealing position. The transfer into the opening position results from an elastic displacement of this base of the substance storage chamber on account of the reduced pressure occurring behind or beneath the piston during the return stroke of the latter. In the process, pulverulent substance drops into the metering chamber. A suction stream refills the substance storage chamber above the filling level by the corresponding volume which has moved into the metering chamber. An air-permeable covering of a hole in the base of the substance storage chamber should on the one hand allow air to pass through as easily as possible in order to expel the powder, but on the other hand in the opposite direction should be such that the reduced pressure lifts the edge of the metering chamber off its sealing seat to a sufficient extent. Here, it is possible to use a filter sheet, consisting of nonwoven or woven material. The pore width is one μ. The powder itself therefore cannot pass through. A first thin layer of the powder which has dropped closes the pores of a material of this type. In a structurally advantageous way, the base and the recess of the substance storage chamber are formed by an elastic cup-shaped membrane, the cup inner wall of which carries an insert part, on the upper edge of which the piston body portion inner tube touches down in a sealing manner by means of a mating closure surface. Metering quantity and substance storage quantity are separated by a cup-shaped membrane of this type when the membrane is closed. Furthermore, it is proposed that the piston has a piston lip which faces in the opposite direction to the direction of the return stroke and engages in a sliding manner against the inner wall of the cylinder. Flow behind the piston lip which is made possible in this way ensures a uniform reduced pressure during the return stroke of the piston. This protects the covering or membrane from tearing or the like. Moreover, an advantageous feature consists in the fact that the permeability of the covering in relation to the fineness of the grains of the powder is such that the thin-layer powder quantity which drops onto the base after the first opening movement of the latter eliminates the air permeability in the opening direction. Then, an advantageous feature consists in the fact that the piston body portion inner tube extends to just before the mouthpiece opening and leaves open, toward the wall of the surrounding piston body portion material, an air inflow passage which extends into the substance storage chamber. This produces an air flow of the reduced pressure source which entrains and also mixes the pulverulent substance. In this context, it is provided that a cover, which is permeable to the inflow air, crosses the piston body portion inner tube in a supporting manner on both sides and has a central hole aligned with the discharge passage, is formed in the upper region of the substance storage chamber. The discharge passage is therefore continuously open; the area surrounding the piston body portion inner tube allows air to pass through but retains the pulverulent substance. Furthermore, it is proposed that the discharge passage narrows in a funnel shape in the direction of flow at the discharge quantity collection location. This increases the region in which the substance is to be drawn, with a centering and accelerating action on the carrier stream. To prevent distorting air from presenting problems during collection of the pulverulent substance to form a metered discharge quantity, a barrier is provided. This consists in a valve body, which opens in the discharge direction, being disposed in front of the central hole. The deformation of the cavity which forms the metering chamber as a result of the reduced pressure during transfer into the opening position of the metering chamber creates a free space beneath the piston body portion inner tube, which is then in communication only with a tightly limited air volume, which air volume extends from the sealing seat edge to the valve barrier. Moreover, an advantageous mode of actuation results through a response threshold for the manually actuated piston displacement. The response threshold allows a defined actuating pressure to form. This is selected such that it can be successfully controlled. If the resistance of the response threshold to be overcome collapses, an accelerated displacement of the piston relative to the housing of the manually actuable inhaler is achieved. In structural detail, this is embodied by the fact that the response threshold is formed by an annular body of the piston body portion on the rear side of the piston sleeve, which annular body latches into a latching groove in the cylinder wall belonging to the piston. Including the annular body which is also involved in forming the resistance, the opening pressure amounts to approx. 2.5 kg. The annular body is expediently an oval spring annulus which in terms of cross section in the clear diameter of the cylinder is accommodated in the region without a latching groove.

An advantageous refinement of the inhaler consists in the fact that the metering chamber is formed by an end-side widening region of the discharge passage, which is set down onto the air-permeable membrane or covering of the base and is lifted off during the spring return stroke. In reality, the opening movement is, of course, executed by the base lifting off. The uniformly flat positioning onto the covering which is tensioned in the manner of a membrane makes it possible to achieve a metering chamber which is no longer, albeit only partially, occupied by the end portion of the piston body portion inner tube constituting the discharge passage, but rather is merely delimited in the style of a miniature hat. This simplifies the structure. Furthermore, it is proposed that the boundary wall of the metering chamber widens conically in the discharge direction. This creates a suitable collecting environment for the metering chamber in the direction of the metering chamber recess. The boundary wall is integrated in an existing component. This is embodied by the configuration whereby the boundary wall of the metering chamber consists of elastic material and is formed integrally with the base of the substance storage chamber. Furthermore, yet another structurally advantageous measure is embodied by two air inflow passages for the substance storage chamber, which run on both sides of the central discharge passage in a common plane with the latter. This opens up the possibility of a slender overall structure, in particular if, furthermore, the air inflow passages are located in the center plane between waist-like supporting surface indentations.

Furthermore, the invention also relates to a manually actuable inhaler for pulverulent substances, in particular medicinal substances, in which, during the manual actuation, a defined discharge quantity from a substance storage quantity is apportioned out in a metering chamber upstream of a discharge passage for the purpose of airborne discharge from a mouthpiece opening at the end of the discharge passage, a piston which generates the discharge airstream, together with a cavity of the piston body portion, forming a substance storage chamber and the metering chamber, a educed pressure which is generated during the return stroke of the piston opening the metering chamber toward the substance storage quantity, and furthermore the base of the metering chamber being formed by an air-permeable membrane, and as a further development proposes that the metering chamber, in the basic position of the piston body portion, be open toward the substance storage chamber. This leaves the filling path open, so that a stroke-independent, temporally extended introduction is achieved for the discharge quantity. Only during the discharge actuation, i.e. in the use phase of the dispenser, does the metering chamber close. Therefore, in the basic position the contact is retained between the discharge quantity retained in the still open metering chamber and the storage quantity located in the substance storage chamber. This may be advantageous for substances which are critical in this respect. The holding-open can be achieved by simple, even available means by virtue of the metering chamber opening toward the substance storage chamber as a result of an idling stroke between the piston body portion and the piston sleeve which forms the metering chamber. With regard to the opening motion, the piston functions as a dragging piston. The metering chamber is opened or closed at the changeover from dragging to pushing or vice versa. The initiator in this context is the frictional lock between piston lip and cylinder wall. Moreover, it is advantageous for the base of the substance storage chamber to be part of the piston sleeve and to rest in a sliding manner against the inner wall of the piston body portion. The base may have a slight prestress in this respect, so that on the one hand the sealing requirement is taken into account and on the other hand so is that of good mobility. Furthermore, the procedure is such that the metering chamber is partially formed from a recess in the piston sleeve and partially comprises a valve cone which is set down in a sealing manner onto the edge of the recess in the metering chamber and narrows in the discharge direction. This valve cone functions as a stationary cover which the movable recess, or more accurately the base, approaches. The idling stroke is spring-triggered and is formed by virtue of a collar of the piston sleeve projecting into a correspondingly axially oriented wide slot on the inner wall of the piston body portion. The metering chamber gap is defined by the opening stroke. In this configuration, the cylinder wall for the piston sleeve is formed by a connection piece of a baseplate. In this context, with a view to creating a spring chamber, it has proven advantageous for a piston spring to extend on the outside of the connection piece, specifically in an annular gap between connection piece and outer wall of the inhaler. With regard to the valve cone, the latter is, for example, also of dome-shaped or pyramid configuration, and furthermore, specifically, such that the valve cone has lips which are cut free and face in the discharge direction and the cut ends of which are thickened. This retains the restoring force and the mobility typical of valve flaps yet nevertheless provides a well-supported, relatively large-area closing contact at the corresponding edges.

BRIEF DESCRIPTION OF THE DRAWINGS

The subject matter of the invention is explained in more detail below on the basis of three exemplary embodiments illustrated in the drawings, in which:

FIG. 5a shows an excerpt from an intermediate position immediately after the base of the substance storage chamber has been sprung out downward, i.e. when the metering chamber has just been opened, illustrating the (theoretical) instantaneous increase in volume of the metering chamber, FIG. 8 shows the inhaler in the actuating position, likewise in longitudinal section, FIG. 9 shows the cross section on line IX-IX in FIG. 8, FIG. 10 shows an enlarged longitudinal section through an inhaler closed off by a cap, representing the spring-loaded basic position of its piston, in accordance with a third exemplary embodiment, FIG. 16 shows a perspective illustration of the valve, formed as a valve cone, FIG. 17 shows an illustration corresponding to FIG. 16 with a pyramid-shaped configuration of the valve, FIG. 18 likewise in schematic form, illustrates the corresponding pyramid shape alone.

DETAILED DESCRIPTION OF THE PREFERRED EMBODIMENT(S)

Figure 1:
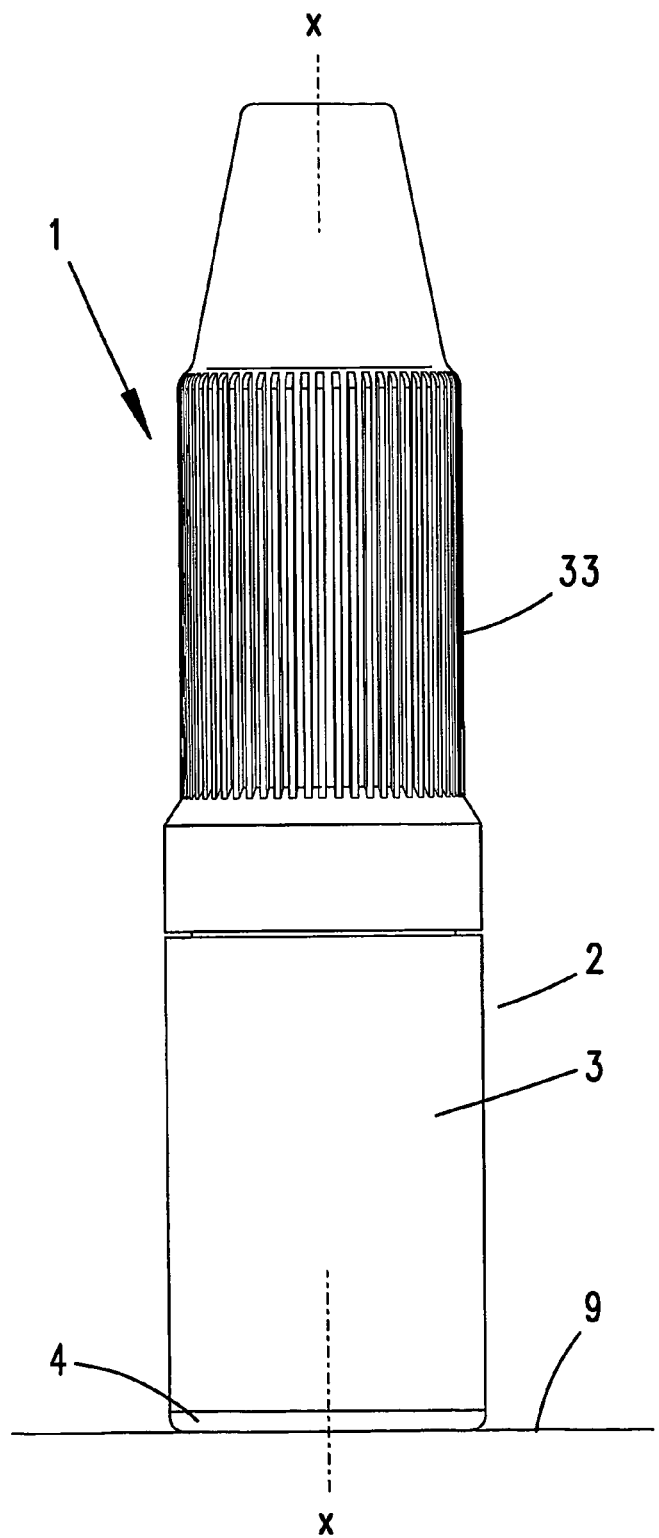
FIG. 1 shows a side view of a manually actuable inhaler, closed off by a protective cap, in accordance with a first exemplary embodiment, on an enlarged scale.
Figure 2:
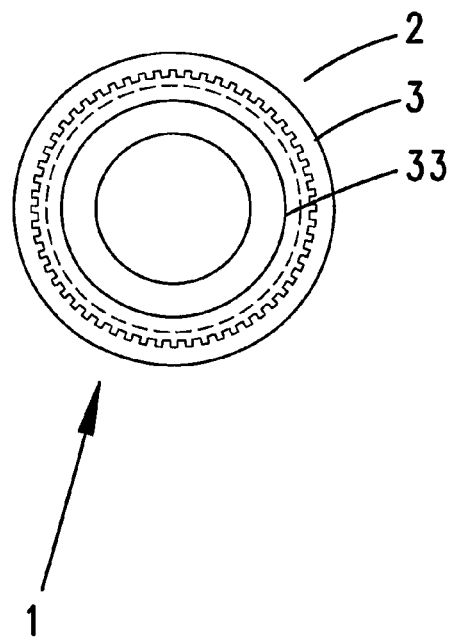
FIG. 2 shows the corresponding plan view.

The inhaler 1 illustrated, which is formed as a pocket device, has a housing 2 which is basically circular in cross section. A cylinder 3 as part of a piston/cylinder unit functioning as a pump forms a component part thereof.

On the base side, the cylinder 3 is tightly closed by a base cap 4. The base cap 4 is clip-fitted into the end region of the cylinder 3 on that side.

The baseplate 4 provides a drying-agent chamber 5. The substance for this purpose is illustrated by small balls 6. The drying-agent chamber 5 is covered by a perforated plate 7 or sealed-on perforated film held in the cylinder 3.

A longitudinally displaceable piston 8 is guided in the cylinder 3 and is realized as a piston sleeve. Its slightly outwardly protruding piston lip 10, which faces in the direction of the standing surface 9, is guided in a sealed manner with a slight prestress against the cylinder wall 11 of the cylinder 3. The piston stroke is defined by end stop means. The orientation of the piston lip 10 leads to the lip 10 being lifted off the wall 11 when a defined reduced pressure is exceeded, with a view to limiting the reduced pressure by the air which then flows into the space beneath the piston 8.

Figure 3:
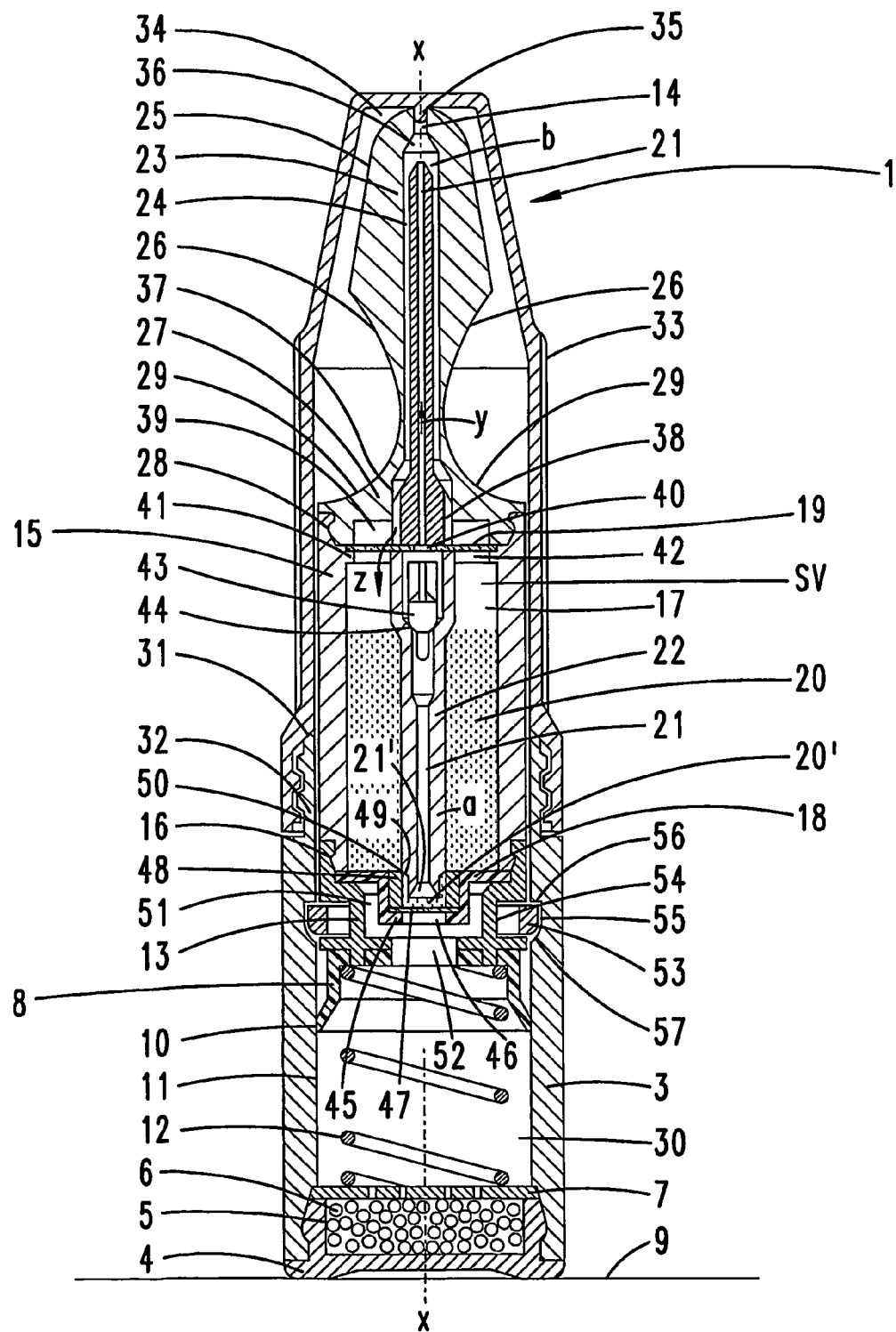
FIG. 3 shows a longitudinal section through the inhaler closed off by a cap, representing the spring-loaded basic position of its piston.

The piston 8 is under spring load in the direction of its basic position (FIG. 3) of the inhaler 1. The spring, a helical compression spring, is denoted by reference numeral 12.

One end spring turn thereof projects into the cavity of the piston 8, i.e. into the cavity of the piston sleeve, while the other butts against the stationary perforated plate 7.

The elastic piston sleeve is seated on a piston head 13 made from a material which is harder in relative terms. The parts 8 and 13 can be produced using the combined injection-molding process. A multi-component injection-molding process is used.

On the side remote from the base, the piston head 13 continues into an upper piston portion 15 running in the direction of a mouthpiece opening 14. This upper portion is of hollow-cylindrical configuration and is fixedly connected to the piston head 13. A corresponding latching location is denoted by 16. Latching bead and latching groove can be seen from the drawing.

A cavity 17 in the piston body portion 15 is used to form a substance storage chamber SV. This chamber is closed off on the piston side by a base 18 and on the mouthpiece opening side by a cover 19.

The substance is a pulverulent, in particular medicinal substance, the storage quantity of which is denoted by 20 in the drawing. Manual actuation of the inhaler 1 separates accurately reproducible discharge quantities 20' from this substance storage quantity 20 in a metering chamber D. The separation is carried out in spatial terms in front of a discharge passage 21, specifically at the lower end a, facing the piston 8, of a piston upper portion inner tube 22. The piston upper portion inner tube 22 is located in the center of the upper portion 15 of the piston 8, which is spring-loaded. The piston upper portion inner tube 22 moves past or penetrates through not only the entire length region of the cavity 17 but also continues into further upper portion material 23 surrounding the piston upper portion inner tube 22.

The geometric longitudinal center axis of the central piston upper portion inner tube 22 coincides with a rotationally symmetrically located longitudinal center axis x-x of the inhaler 1. To this extent, the storage quantity 20 is located in an annular space, on emerging from which the discharge quantity 20' is collected beneath the piston-side end a of the upper portion inner tube 22, for the purpose of subsequent discharge from the mouthpiece opening 14 at the other, i.e. upper, end b of the discharge passage 21.

The piston upper portion inner tube 22 extends as far as just in front of the mouthpiece opening 14. The lateral surface region of the upper portion inner tube 22 is surrounded, leaving the radial spacing, by the piston upper portion material 23, more specifically its wall, so that an annular space remains over the entire length of the upper portion material 23. This constitutes an air inflow passage 24 disposed concentrically with respect to the discharge passage 21. This air inflow passage 24 extends as far as into the substance storage chamber SV and is connected to atmosphere via mouthpiece opening 14. 14 is, as it were, also a breathing hole, in particular in order to compensate for the reducing volume of powder.

The piston upper portion material 23 is a club-shaped extension 25 of the upper portion 15. Its free end converges frustoconically so as to form a rounded head portion in the region of the mouthpiece opening 14. A connection piece of this type can be inserted in a correctly guided manner into, for example, one of the user's nostrils.

Indentations 26 are located at the base of the extension 25. These indentations, the bases of which face one another, merge after a concave contraction into a broad pedestal 27. Once again, a latching location, denoted by 28, is incorporated between the pedestal 27 and that end of the piston upper portion 15. This latching location likewise has a latching bead and a matching latching groove, as is evident from the drawing.

Figure 4:
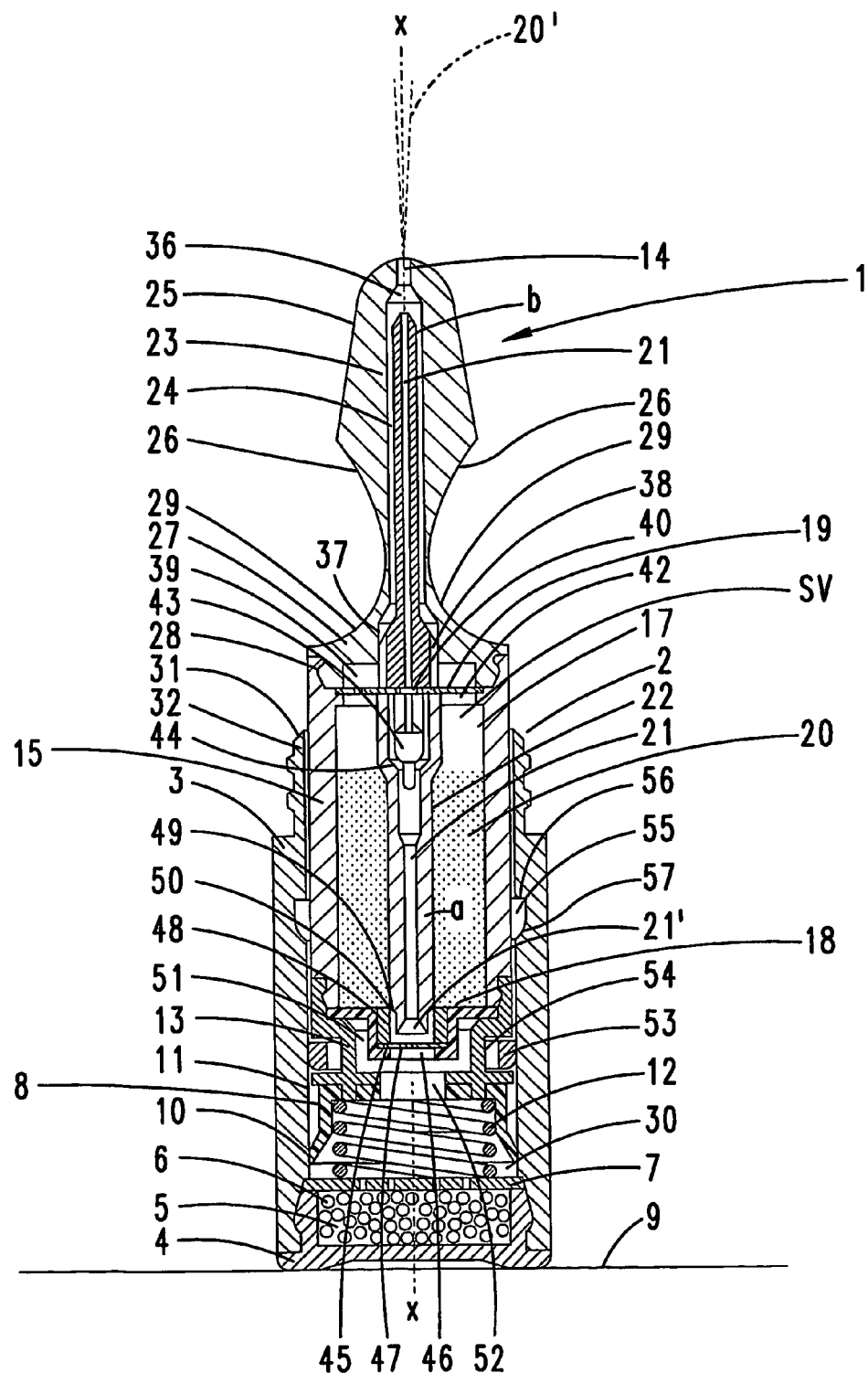
FIG. 4 shows the inhaler in the actuating position, likewise in longitudinal section.

The shoulder-forming portion of the club-shaped extension 25, on account of the indentations 26, makes it possible to form finger support surfaces 29 on the pedestal 27, via which the piston 8, via piston upper portion 15, can be displaced counter to spring load into the position shown in FIG. 4.

The cylinder space 30 of the piston 8 has an axial length which approximately corresponds to the piston diameter. The end portion of the piston upper portion 15 on the mouthpiece opening side axially projects above a neck edge 31 of the cylinder 3 by at least this dimension. The neck edge 31 is the upper termination of a neck part 32 of the cylinder 3. The lateral surface of the neck part 32 bears an external screw thread which interacts with a mating internal screw thread of a threaded base of the protective cap 33 of the inhaler 1. The lateral surface of the protective cap 33 may be roughened, in particular longitudinally fluted, in order to facilitate actuation of the screwing motion.

A closure stopper 35 starts, on the inner side of a flattened cover of the protective cap 33, from a dome 34, which converges on the discharge side, of said protective cap 33. This closure stopper 35, if the device is closed correctly, moves into the mouthpiece opening 14 in such a manner as to form a sealing closure.

Beneath said mouthpiece opening 14, an intermediate chamber 36 is left clear between the corresponding exit of the discharge passage 21 and the start of the mouthpiece opening 14, so as to form an opposite flow diverter for the air inflow passage 24 on the one hand, and the discharge passage 21, on the other hand. The end of the piston upper portion inner tube 22 tapers to a point. This forms an inclined guide shoulder for the inflow air.

In the plane of the pedestal 27, the air inflow passage 24 adopts a slight inclination. There, the wall of the piston upper portion inner tube 22 is slightly thickened. The thickened region is seated in a mating recess 37 in the pedestal 27. A frictionally locking plug connection is present, with two or more longitudinally running grooves 38 being formed such as to produce a passage. The grooves 38 lead to a free space 39 above the cover 19.

At the level of the cover 19 the body of the piston upper portion inner tube 22 is interrupted, but not in terms of flow. This manifests itself by the fact that a cover 19 which is permeable to the inflow air and crosses the piston upper portion inner tube 22 so as to provide support on both sides, is formed in the upper region of the substance storage chamber SV. By contrast, above the vertically crossing extension of the discharge passage 21, the cover 19 has a hole 40. The corresponding permeability is offered, for example, by a filter paper.

Figure 6:
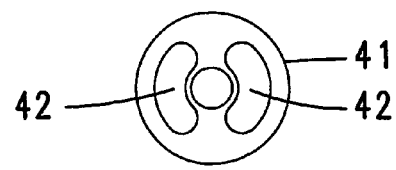
FIG. 6 shows a detail of the supporting of the cover of the inhaler.

The cover 19 is supported by a perforated holder 41 which leaves throughflow openings 42. These may be web-spaced arcuate openings (cf. FIG. 6). The web material close to the piston upper portion forms a reliable support for the cover 19, which at the top side is clamped in at the edge by an annular collar at the latching location 28 against the holding means 41.

A clamping holding arrangement of the same type is also realized close to the holes, as a result of the widened ends of the two-part piston upper portion inner tube 22 moving onto one another in the crossing region of the cover 19. That part of the inner tube 22 which is received in the cavity 17 is integral with the piston upper portion 15 via the holding means 41.

In front of the central hole 40 is a valve body 43 which interacts with a valve seat surface 44. A nonreturn valve of this type opens in the discharge direction but closes when the air flows in via the passage 21. The substance-carrying stream flushes around the nonreturn valve. The associated valve chamber is achieved by corresponding widening of the tube end there. The valve stem of the valve body 43 has crossing wings which, however, cannot keep the hole 40 closed in the core during air discharge.

The discharge quantity 20' which is to be divided off from the substance storage quantity 20 collects in a metering chamber recess 45 in the base 18 of the substance storage chamber SV. This consists of a body made from elastically flexible material configured in the shape of a hat or cup. The hat edge is clamped in at the edge in the region of the latching location 16, in a similar way to what has been described above with regard to the cover 19.

The base 18, or more specifically the surface of the body which is inserted or configured in the shape of an inverted hat, has a centrally located hole 46. This hole 46 has an air-permeable membrane or covering 47. The structure of the corresponding filter material is such that the pulverulent substance cannot pass through in both cases, but rather, as has already been stated, only air can do so, and then only in the direction of the mouthpiece opening.

The cup inner wall of the cup- or hat-shaped body carries a sleeve-shaped insert part 48, acting, as it were, as a reinforcement at the cup inner wall. The end a of the piston upper portion inner tube 22, in the basic position, is seated in a sealing manner on the upper, inner edge of this insert part. This occurs on account of the restoring force inherent to the base 18. Said edge is denoted by reference numeral 50. The end-side mating closure surface at the stationary inner tube 22 is denoted by 49. This mating closure surface is realized as a frustoconical zone which continues into an end piece of reduced external diameter which is funnel-like in form in the opposite direction. The reduced end piece also penetrates into the cup portion. The end piece constitutes the mouth leading to the discharge passage 21. This optimizes the discharge of the substance. The funnel 21' narrows in the mouthpiece direction. This results in the airborne pulverulent substance being compressed in the form of a bell so that it is accelerated in terms of flow in the narrower passage portion. A powerful jet is formed, which transports the medicament even into nasal sinuses. On the other hand, however, there is no sudden blast of flow which may be considered unpleasant. For this purpose, the air quantity is limited. In this context, it has proven advantageous for the airstream volume which results from the piston movement to amount to more than one hundred times but less than six hundred times the volume of the metering chamber D. For example, approx. 10 mg of pulverulent substance are distributed in 4 ml of airstream. The volume of the metering chamber is 10 mm³. The pore width of the air-permeable membrane or covering 47 is set to approx. 1μ. A formula of this type is also expedient with regard to the mechanical load-bearing capacity of the dispenser mechanism, and consequently, the service life of the device is satisfactory.

The recess 45, i.e. the cup part of the base 18 which surrounds it, projects into a recess 51 in the piston head 13 over the distance required for the movement. The basis here too is a cup shape with radial and axial yielding play for the base 18. Piston head 13 and piston 8 are provided with a central aperture. The corresponding opening is denoted by reference numeral 52. In terms of flow, it is connected to the cylinder space 30 of the pump, which is thereby connected to the recess 51.

With a view to the displacement of the piston 8 using the extension 25 as an actuating handle, a response threshold for the manually actuated piston displacement is given to the inhaler 1. A resilient annular body 53 is a component part of this initial support which yields in the event of overload. This annular body is connected to the piston upper portion 15 on one side. For this purpose it is seated in an annular groove on the neck-like part 54 of the piston head 13. Said annular body 53 is thereby axially retained thereon. It projects, by way of two diametrically opposite protruding zones, into a latching groove 55 located in the cylinder wall 11. The latching groove 55 has an upper, steep flank 56 and a lower flank 57 which falls away in the inward direction. The flank 57 suddenly diverts inward the bowed-tongue-like protruding zones forming the response threshold, so that the locking action suddenly ceases. The piston 8 is suddenly displaced so as to compress the air located in the cylinder space 30. The opening pressure on the spring 12 as well as annular body 53 is approx. 2.5 kg. This is a level which can deliberately be applied in the range which can be optimally managed in ergonomic terms. Once it has been released again, the annular body 53 snaps back into the latching groove 55 in a blocking manner. This is the stop-limited basic position; the annular body 53 bears against the steeper flank 57.

The inhaler 1 functions as follows: by positioning the fingers of the actuating hand on the finger support surfaces 29 and using the thumb for counter-support of the baseplate 4 commensurate with the holding grip, it is possible, using such a holding grip, for the piston 8 to suddenly move downward, counter to spring loading in the manner which has been described. The air undergoing compression located in the cylinder space 30, the volume of which is being reduced, bursts through the air-permeable membrane or covering 47 into the metering chamber D, which is blocked off with respect to the storage quantity 20 and in which the discharge quantity 20' has been held ready from a preceding actuation. The result is a powerful yet damped expulsion of the pulverulent substance, carried by the airstream, to the target location, for example, above the nasal cavity. In the process, the valve body 43 is lifted off the valve seat surface 44. A sealing closure is present between the surface 49 of the piston upper portion inner tube 22 and the corresponding edge 50. The discharge of the quantity 20' which has been divided off is position-independent.

Figure 5B:
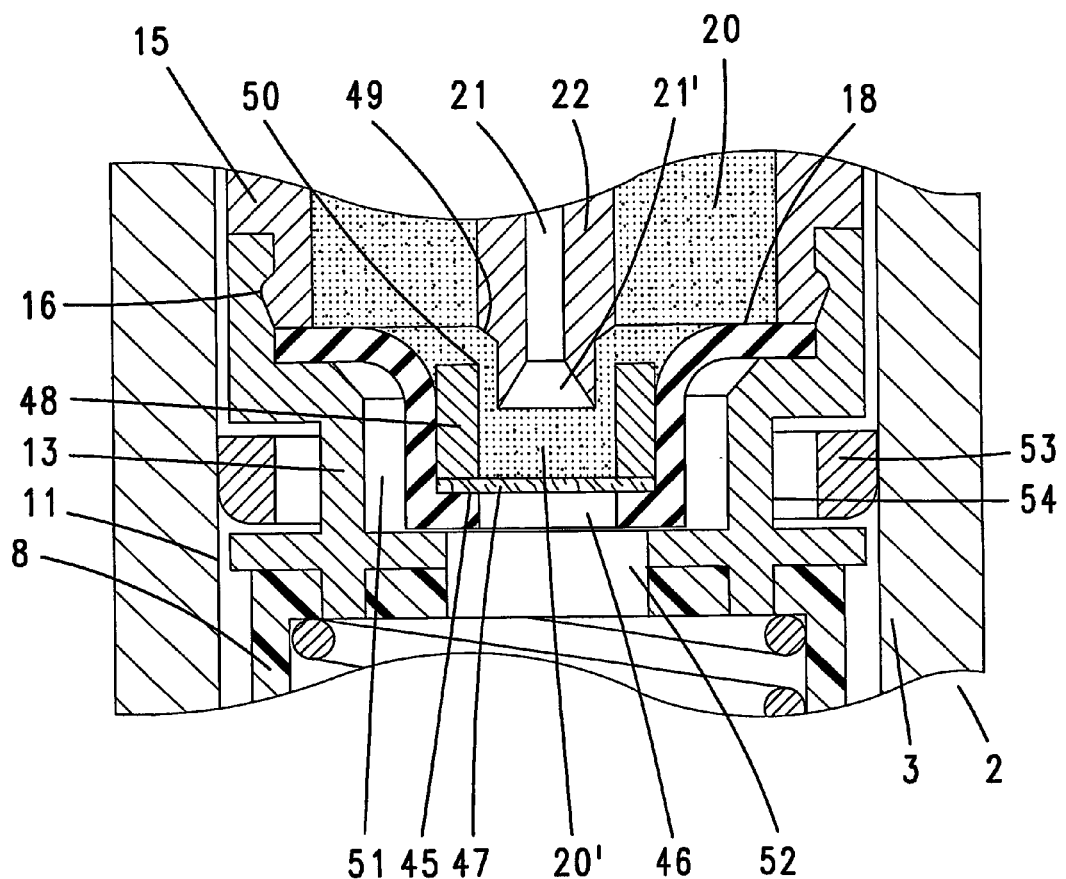
FIG. 5b shows a later intermediate position, with the metering chamber already having been refilled.

If the user releases the actuating position of the inhaler 1, the piston 8, under the spring force of the spring 12 moves back into its basic position. This increases the volume of the pump chamber, i.e. of the cylinder space 30. The hat-shaped body, the base 18, is pulled downward, counter to its elastic restoring force, by the reduced pressure which then prevails, into the position shown in FIG. 5*a*: the (empty) metering chamber D which is responsible for apportioning off the powder is open toward the substance storage chamber SV. The metering chamber D is refilled, i.e. an accurately metered discharge quantity 20' moves out of the storage quantity 20 into the metering chamber D, partially by virtue of its own weight and partially through mass inertia, and partially through the increase in the chamber volume as a result of the downward pulling of the cup-shaped body and, depending on the extent of the air permeability, of the membrane or covering 47 in the downward direction, boosted by an airflow in the direction of the covering or membrane 47, but in particular on account of the increase in volume resulting from this downward movement. The first, very thin layer of the powder closes the pores in the covering 47, so that the opening position is initially retained. The travel of the elastic displacement of the base 18 into the opening position of the substance storage chamber SV is limited by the fact that during the return stroke of the piston 8 the reduced pressure which occurs behind or more specifically beneath the piston, is limited by the downwardly directed lip 10 of the piston 8, which in the event of an excessive reduced pressure is lifted off from the wall 11 so as to perfectly compensate for this by admitting air to the space 30. The suction stream lifts the edge 50 off the mating surface 49 of the end a of the piston upper portion inner tube 22 for as long as the reduced pressure exists. Perfect filling takes place (FIG. 5*b*). The pulverulent substance is retained with respect to the cylinder space 30 by the air-permeable membrane or covering 47. There is no disturbance to the discharge quantity 20', in particular because the substance always remains loose. When the piston 8 is back in the raised position (FIG. 3), the base 18, on account of its elastic restoring action, moves back into the closed position shown in FIG. 3, which upward movement also promotes uniform, full filling of the metering chamber D. The edge 50, which in each case alternates between a sealing position and an opening position of the piston upper portion inner tube 22, always reliably moves into the sealing position which closes the metering chamber D which is responsible for apportioning off, especially since any excess pressure in the passage 21 can escape.

The discharge flow is denoted by arrow y and the inlet flow is denoted by arrow z.

The latching location 28 may be configured such that it can be opened as a filling access.

The manually actuable inhaler 1 in accordance with the second exemplary embodiment corresponds in principle and as far as possible also in structural terms to the basic version which has been described in detail and is embodied in the first exemplary embodiment. The reference symbols are transferred accordingly to the extent that they are required in order to gain an understanding, in some cases without the associated text being repeated, since the corresponding disclosure content can be read onto the basic version.

Figure 7:
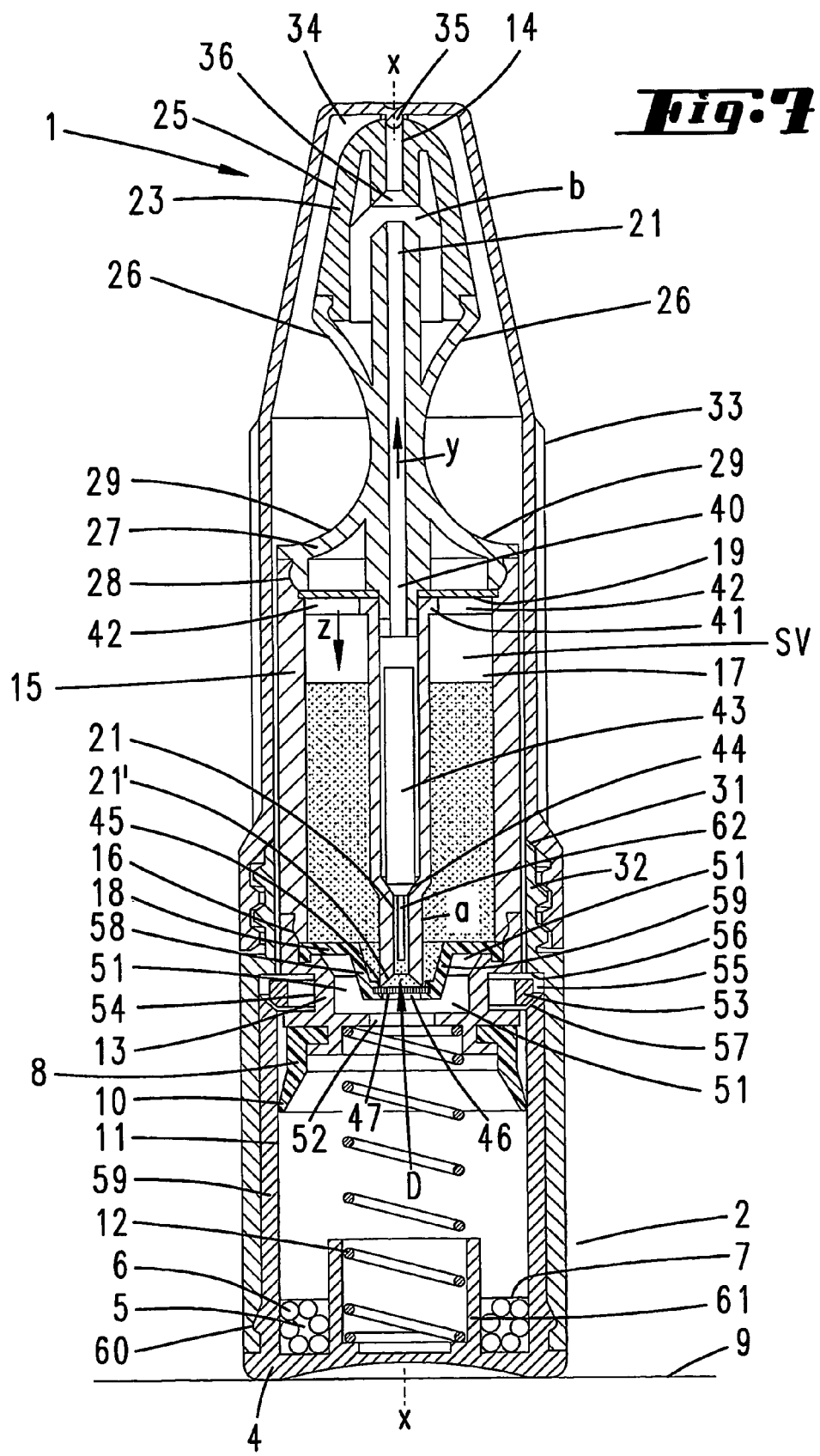
FIG. 7 shows a longitudinal section through a cap-closed inhaler, representing the spring-loaded basic position of its piston, in accordance with a second exemplary embodiment, on an enlarged scale.

Beginning with FIG. 7, the metering chamber D has been modified. Instead of forming the mating closure surface 49 at an axially recessed portion of the lower end a of the piston upper portion inner tube 22, this mating closure surface is now produced directly by the hollowed end face of said piston upper portion inner tube 22. In terms of the specific solution, this is embodied by the fact that the metering chamber D is now formed by an end-side widened region of the discharge passage 21 which is seated directly on the air-permeable membrane or covering 47. The discharge passage 21, which is seated in an abutting manner in this way, during the spring excursion of the spring 12 as described, is lifted off from the stationary, lid-like widened region which is, as it were, outwardly bulbous. In geometric terms, this widened region is in this case too a funnel 21'. Of course, the restorable base 18, which is elastic in this case too, and into which the air-permeable membrane or covering 47 is formed, is moved in the downward direction and is lifted off. For this purpose, the area surrounding the body, which in this case too is in the shape of a cup, is provided by a recess 51 which provides free space in the axial direction and in the radially outward direction.

The periphery of the base 18 has a vertical rotationally symmetrical angled-off portion, which is securely retained in the region of the latching location 16 between the upper portion 15 and the piston head 13 provided in this case too.

A boundary wall 58 of the base 18, surrounding the metering chamber D so as to form said cup-shaped configuration, is specifically in this case frustoconical in form. This structure, which is similar to that of a flower pot, is such that the boundary wall 58 of the metering chamber D widens in the discharge direction, as evidenced by arrow y relating to the discharge flow.

The boundary wall 58 of the metering chamber D also consists of elastic material and is formed integrally with the base 18 of the substance storage chamber SV.

The frustoconical boundary wall 58 maintains a fillable spacing with respect to the corresponding lateral wall of the end a of the piston upper portion inner tube 22. The annular zone, which, as it were, points to the rear in a rotationally symmetrical manner, provides an advantageous collection channel directly at the foot of the funnel-shaped cover of the metering chamber D.

The edge, which protrudes outward in the style of annular ribs and is put in place with respect to the air-permeable membrane or covering 47, of the funnel 21' has a diameter which substantially corresponds to that of the hole 46 of the metering chamber recess 45.

In this case too, the parameters relating to the volume of the metering chamber D and to the airstream volume delivering the pulverulent substance are the same. In structural terms, it should also be noted that the cylinder wall 11 is now no longer provided by the cylinder 3 which already partly forms the housing 2 but rather by the baseplate 4. A connection piece 59 protrudes from the latter. The connection piece 59 is inserted into the housing 2 from below with latching securing. Leaving clear an axial spacing, it extends in front of the shoulder, which merges into the neck 32, of the housing 2. The latching location which secures the interengagement is denoted by reference numeral 60 and comprises the standard latching bead and a matching latching groove.

Said axial spacing with respect to the said shoulder is now utilized with a view to providing a latching groove 55 for the annular body 53, in this case too, representing the steep flank 56 and the falling-away flank 57. The latter is the funnel-shaped end of the connection piece 59.

In a central location, the base cap 4 is used to form a spring chamber for the spring 12, which in the present case is likewise realized as a helical compression spring. An annular wall 61 leads from the cap base 4 so as to form a chamber. The metering-side end face of the annular wall 61 functions as a limiting stop for the piston head 13. Hard part meets hard part.

In the subject matter in accordance with the second exemplary embodiment, the drying-agent chamber 5 is now configured as an annular chamber, accommodating the covered balls 6, now in the form of an annular perforated plate 7 or film.

With regard to the actuation region of the inhaler 1, the same structures are employed here. Just one difference with respect to the basic version is that the central inflow passage 24 has now been replaced by a double passage as air-conducting means for the pressure compensation in the powder reservoir, i.e. storage quantity 20. Reference should be made to FIG. 9, from which it can be seen that the two air inflow passages, likewise denoted by 24, are located in the center plane between supporting surface indentations 26 which form or are in the shape of a waist. The passages 24 extend on both sides of the central discharge passage 21 in a common plane. They have a larger cross section than that of the central discharge passage 21. The ratio is approximately 2:1. Fitting bores of this type in a common plane makes it possible to form the indentations 26 such that they cut into a greater depth so that finger support surfaces 29 of correspondingly larger area are formed as a result.

The functioning and operating mode of the valve body 33 correspond to the basic version, except that the valve seat surface 44 is now closer to the base 18 of the substance storage chamber SV and the valve body 33 overall is of longer configuration.

Moreover, on the base side, the valve body 43 continues into a centering pin 62 which projects into the smaller cross section portion of the piston upper portion inner tube 22.

With regard to the manually actuable inhaler 1 in accordance with the third exemplary embodiment (FIG. 10), the functional and structural configuration thereof is within the described scope of the exemplary embodiments given above. In this case too, the reference symbols are applied accordingly, in some cases without the associated text being repeated, since it can be read from the solutions which have been explained above.

One difference which constitutes a further development consists in the way in which the piston is arranged to control the opening and closing movement of the metering chamber D. Unlike in the previous examples described above, the metering chamber D, in the spring-loaded basic position of the piston upper portion 15, is opened toward the substance storage chamber SV. This leaves the filling path into the chamber D open, so that during handling, positioning, etc. of the inhaler 1, the pulverulent substance preferably collects, simply under the force of gravity. The metering chamber D only closes during the discharge actuation, specifically, as it were, in a gently touching manner, while the excess stock of pulverulent substance is, as it were, displaced away. This is also supplemented by the advantageous action of compression. This provides exactly reproducible discharge quantities 20' of pulverulent substance, specifically using the powder particle quantity/airstream volume ratios, with the base of the metering chamber D, moreover, being formed by the air-permeable membrane or covering 47.

To correspondingly keep the metering chamber D open, the piston 8 or the entire piston sleeve is realized as a dragging piston Sch.

Figure 11:
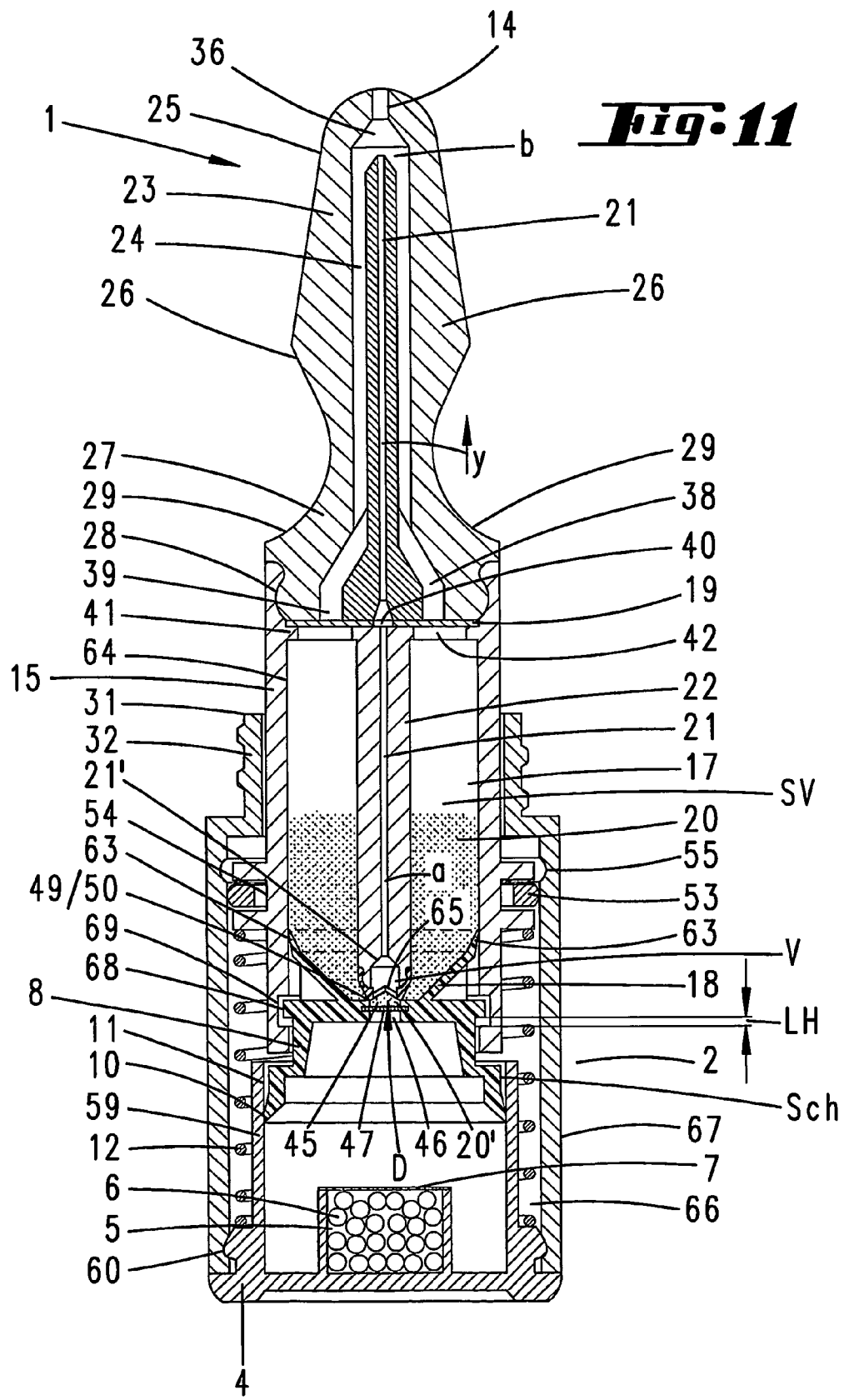
FIG. 11 shows the inhaler in the actuating position, specifically in the initial phase, likewise in section.
Figure 12:
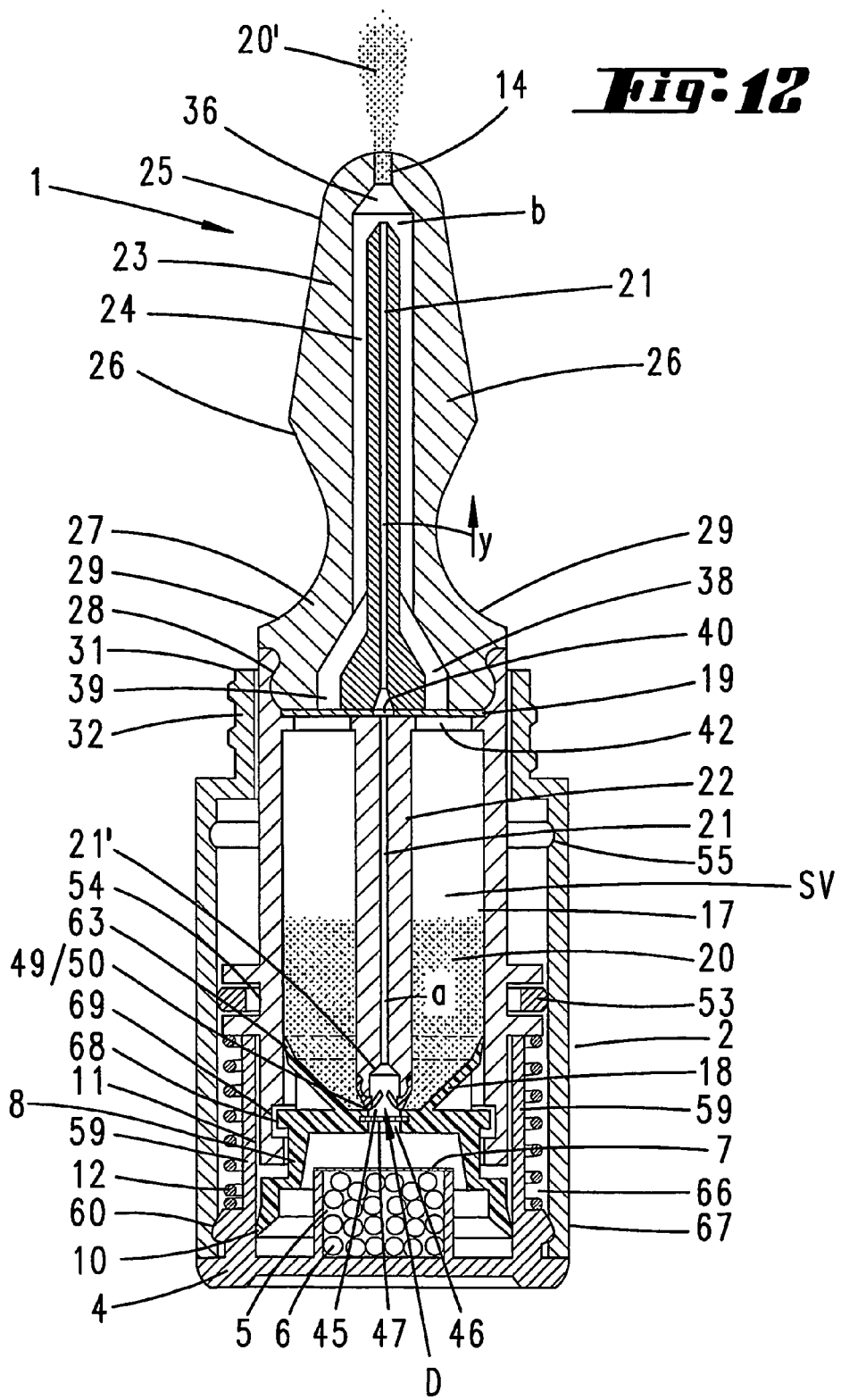
FIG. 12 shows the inhaler in the actuating position, specifically now in the end phase, likewise in longitudinal section.
Figure 13:
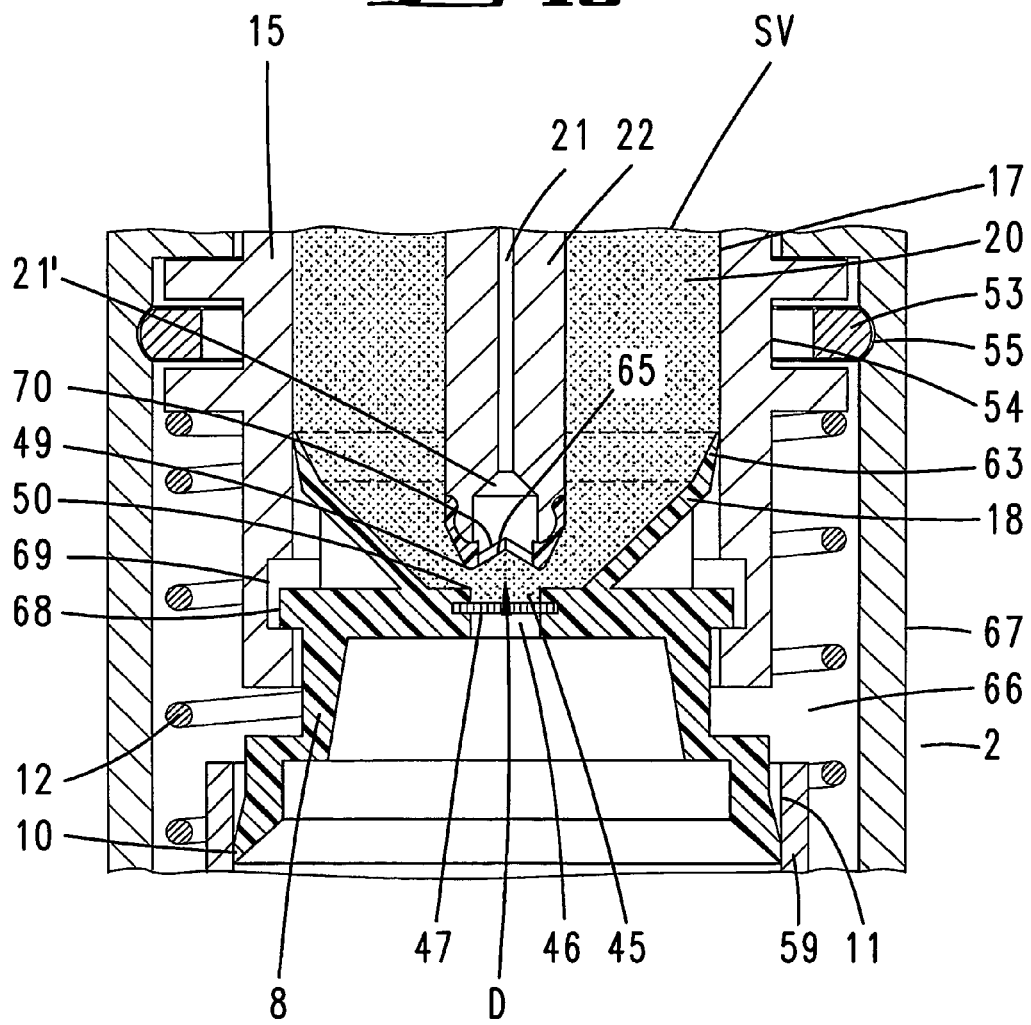
FIG. 13 shows an enlargement of the region of the metering chamber, specifically in the position in accordance with FIG. 10, representing the basic position.

Corresponding switching results from a change from dragging mode to pushing mode, which leads to opening or closing. In structural terms, this is managed by the metering chamber D opening toward the substance storage chamber SV as a result of an idling stroke LH between the upper portion 15 and the piston sleeve which forms the metering chamber. A corresponding play between the two parts forming the piston can be seen from FIG. 11. For the overall size on which the inhaler 1 is based here, the opening stroke amounts to 0.3 mm. Therefore, a corresponding spacing is also present between the valve-reinforced mating closure surface 49 of the piston upper portion inner tube 22 and the corresponding edge 50 of the piston. In the actuating position, by contrast, the metering chamber D closes, as can be seen from FIG. 11.

To achieve the dragging piston function explained above, the base 18 of the substance storage chamber SV and/or the cavity 17 in the piston upper portion 15 which partially forms this chamber and the piston 8 are fixedly connected or integral, substituting for the piston head realized as a hard part. In practice, this is incorporated into the overall formation.

The base 18, which therefore forms part of the piston sleeve, is guided in a sliding manner by way of a lip 63 which is inclined in the discharge direction, against the corresponding inner wall of the piston upper portion 15, which now performs the guide-cylinder-like role. The piston 8 is frictionally locked between the parts 10 and 11.

The base 18 adjoins the lip 13, which is inclined at an acute angle, as an oblique wall. At a spacing from the metering chamber, this oblique wall is rooted in the back of the piston 8. The result is a funnel with a centering action with respect to slipping access of the pulverulent substance. The back of the piston 8 in this respect runs in a flat plane, i.e. perpendicular to the longitudinal center axis x-x of the inhaler 1.

The piston 8 which forms part of the base 18 in this case too has a recess 45 with respect to the metering chamber. At the top, i.e. as seen in the discharge direction, this recess 45 ends in the edge 50 which cooperates with the mating closure surface 49 of a valve cone 65. The latter is a component part of a valve V which consists of rubber or the like and is fitted in a latching manner onto the lower end a of the piston upper portion inner tube 22. The valve cone 65 may actually be a cone or may be a pyramid-shaped body. The more conical configuration can be seen from FIG. 16, whereas the more pyramid-shaped configuration can be seen from FIGS. 17 and 18. The valve V engages over the recess 45, which constitutes a component part of the metering chamber D, the spatial volume of the hollow cone side being connected as a supplementary part protruding beyond the plane of the piston back. The valve V therefore contributes a superstructure which is filled in to the tip, fed from the annular surroundings. The result is that the discharge quantity 20' separated from the storage quantity 20 is, as it were, "stamped out". The branching off from the storage quantity is complete when the actuation commences, specifically right at the outset at the beginning of the stroke, as can be seen from FIG. 11. During this closure, which takes place through downward displacement of the piston upper portion 15, the valve V pushes the piston 8 in front of it, with the frictional lock exerting a braking action. The resistance—as has already been indicated above—is produced via the lip 10, which slides with a gentle prestress over the cylinder wall 11. As can be seen, the conditions with regard to the formation of the cylinder wall 11 here are the same as have been described with regard to the second exemplary embodiment. The reference numerals are applied accordingly. However, the connection piece 59 which is integral with the baseplate 4 is now positioned in such a way that its lateral surface delimits a peripheral spring chamber 66 in which the spring 12 is accommodated, guided between said connection piece 59 and the outer wall 67 of the housing 2.

If the piston upper portion 15 is released, the spring 12 drives the upper portion 15 into the basic position which can be seen from FIG. 10, in which the annular body 53, which is retained directly in a neck part 54, in this case of the upper portion 15, snaps back into the latching groove 55 of the response threshold, with stop limiting by a protuberance of the housing 2. The protuberance is the shoulder between the outer wall 57 and the neck part 32.

The metering chamber D is open and is in this way filled with pulverulent substance on account of the reduced pressure produced behind the piston 8 in the manner described. The piston 8 is held in the dragging position. Its displacement relative to the piston upper portion 15, which makes the idling stroke LH usable, results from the engagement of a collar 68 of the piston sleeve into a slot 69 of corresponding width at the piston-side end of the inner wall of the piston upper portion 15. The carrying-along action is effected via the lower flank of said slot 69. The upper flank of the slot 69 is at a spacing from the back of the piston sleeve, which forms the base, this spacing being greater than the axial idling stroke LH. It is also possible to fit a stop of the same travel between the location described and between edge 50 and mating closure surface 49. However, the arrangement between the collar 68 and the slot 69 is preferred.

The metering chamber D, which is formed partially from the recess 45 of the piston sleeve and partially from the touching down of the cavity of the valve cone 65, is filled up right into the narrowing tip of the cavity of the valve cone when the valve V touches down. On the other hand, however, the closure pressure is also not suitable for opening on account of the compressed substance; rather it requires the described actuation of the device.

Figure 14:
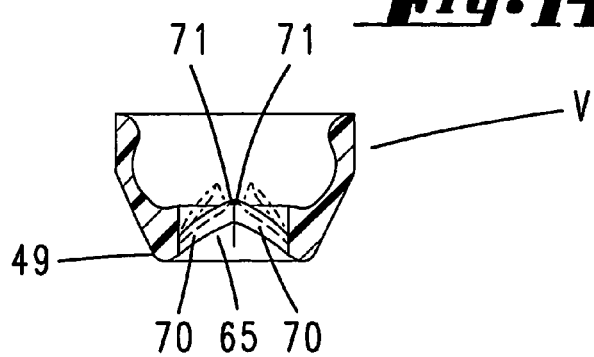
FIG. 14 shows an isolated reproduction of the valve.
Figure 15:
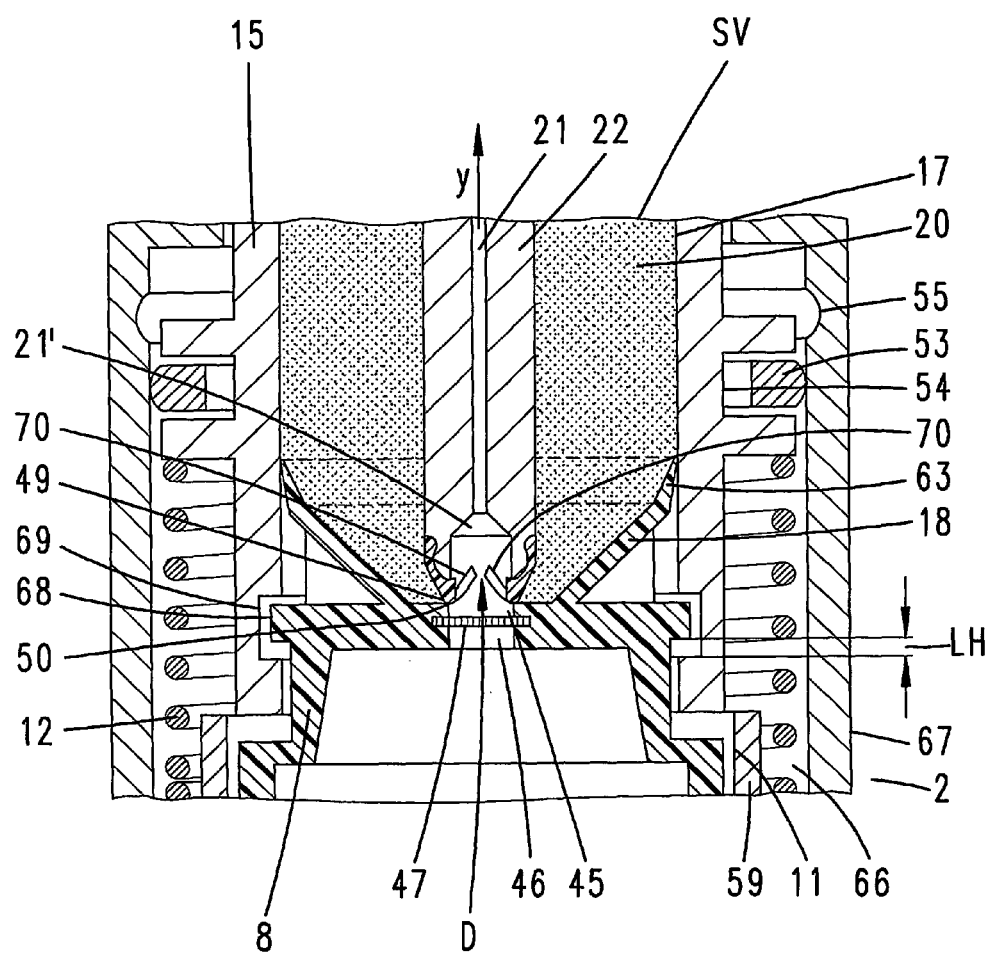
FIG. 15 shows an enlarged partial view of the region of the metering chamber with the valve open for discharge purposes.

With regard to the valve cone 65, it should also be mentioned that the latter, in view of its valve flap 70, which is created, for example, by a cross-cut and acts in the manner of a nonreturn valve, always has a reliable opening and closing behavior. Furthermore, the valve flaps 70 are thickened with respect to their lips 71 which form a point facing in the discharge direction. The lips 71 touch one another over a larger area than the thickness of the valve flaps 71. The incision locations can correspondingly complement one another in terms of their shaping. To form the lips 71, the rear region thereof may, for example, be hollowed out, as can be seen, for example, from FIG. 14.

To create a sufficient free opening space for the valve flaps 70, that portion of the discharge passage 21 which extends in the discharge direction arrow y is cylindrically opened out to a sufficient extent to merge into the funnel 21' described in connection with this cavity of larger cross section.

The plug-fitting assembly between piston 8 and upper portion 15 is facilitated by the inherently elastic material of said piston. Measures which promote plug connection in the form of conventional run-up slopes may additionally be borne in mind (not shown).

The device which has been referred to above as an inhaler and in which, therefore, in principle a substance is discharged in atomized form carried by air, may also be used for other applications, for example as an applicator, powder-metering device, powder sprayer or the like, and even as an atomizer for dyes and poisons.

The invention claimed is:

1. Manually actuable inhaler (1) for pulverulent substances, in particular medicinal substances, in which inhaler, during the manual actuation, a defined discharge quantity (20') from a substance storage quantity (20) is apportioned out in a metering chamber (D) of the inhaler upstream of a discharge passage (21), for the purpose of providing an airborne discharge from a mouthpiece opening (14) of the inhaler at an end (b) of the discharge passage (21), wherein the inhaler further comprises a piston (8) which generates the discharge airstream, together with a cavity (17) in a body portion (15) of the piston, the cavity forming a substance storage chamber (SV) and the metering chamber (D); wherein a reduced pressure, which is generated during a return stroke of the piston (8) opens the metering chamber (D) toward the substance storage quantity (20), the base of the metering chamber (D) is formed by an air-permeable membrane, and the metering chamber (D), in a basic position of the piston body portion (15), is open toward the substance storage chamber (SV), wherein the metering chamber (D) is partially formed from a recess (45) in a sleeve of the piston and partially comprises a valve cone (65) which touches down in a sealing manner onto an edge (50) of the recess (45) in the metering chamber (D) and narrows in the discharge direction.

2. Inhaler according to claim 1, wherein the metering chamber (D) opens toward the substance storage chamber (SV) as a result of an idling stroke (LH) between the body portion (15) of the piston and a sleeve of the piston which forms the metering chamber (D).

3. Inhaler according to claim 2, wherein the base (18) of the substance storage chamber (SV) is part of the piston sleeve and rests in a sliding manner against the inner wall of the piston body portion (15).

4. Inhaler according to claim 1, wherein the valve cone (65) has lips (71) which are cut free and face in the discharge direction, the cut ends of which lips are thickened.

* * * * *